US008079958B2

(12) United States Patent
Satoh et al.

(10) Patent No.: US 8,079,958 B2
(45) Date of Patent: Dec. 20, 2011

(54) ULTRASONIC DIAGNOSTIC APPARATUS, DATA MEASUREMENT METHOD, AND DATA MEASUREMENT PROGRAM

(75) Inventors: Yoshiaki Satoh, Kaisei-machi (JP); Tsuyoshi Shiina, Tsukuba (JP)

(73) Assignees: Fujifilm Corporation, Tokyo (JP); The University of Tsukuba, Tennodal, Tsukuba ( * ) Notice: Subject to any disclaimer, the term of this patent is extended or adjusted under 35 U.S.C. 154(b) by 603 days.

(21) Appl. No.: 12/029,901

(22) Filed: Feb. 12, 2008

(65) Prior Publication Data

US 2008/0196506 A1 Aug. 21, 2008

(30) Foreign Application Priority Data

Feb. 15, 2007 (JP) ................................. 2007-034918

(51) Int. Cl.
*A61B 8/00* (2006.01)

(52) U.S. Cl. ......... 600/443; 600/407; 600/437; 382/128

(58) Field of Classification Search .................. 600/437, 600/407, 443; 382/128
See application file for complete search history.

(56) References Cited

U.S. PATENT DOCUMENTS

| 7,686,764 B2 * | 3/2010 | Watanabe et al. ............. 600/443 |
| 2006/0190875 A1 * | 8/2006 | Arisawa et al. .................... 716/5 |
| 2009/0024032 A1 * | 1/2009 | Kato et al. ..................... 600/443 |

FOREIGN PATENT DOCUMENTS

| JP | 2889568 B1 | 2/1999 |
| JP | 2005-118314 A | 5/2005 |

OTHER PUBLICATIONS

Hiroyuki Toide, "Proper Ultrasonic Examination of Blood Vessels", Ultrasonic Examination Technique, 2006, p. 80, vol. 31, No. 2.

* cited by examiner

*Primary Examiner* — Tse Chen
*Assistant Examiner* — Joel F Brutus
(74) *Attorney, Agent, or Firm* — Sughrue Mion, PLLC

(57) ABSTRACT

An ultrasonic diagnostic apparatus by which IMT examination can be efficiently performed by simple processing in a health check. The ultrasonic diagnostic apparatus includes: a signal processing unit for performing at least envelope detection processing on reception signals outputted from an ultrasonic probe to generate envelope data; an image data generating unit for generating image data representing an ultrasonic image on an object to be inspected based on the envelope data; a pre-measurement processing part for performing structural image generating processing on the envelope data; and a measurement part for performing measurement based on the envelope data processed by the pre-measurement processing part.

9 Claims, 15 Drawing Sheets

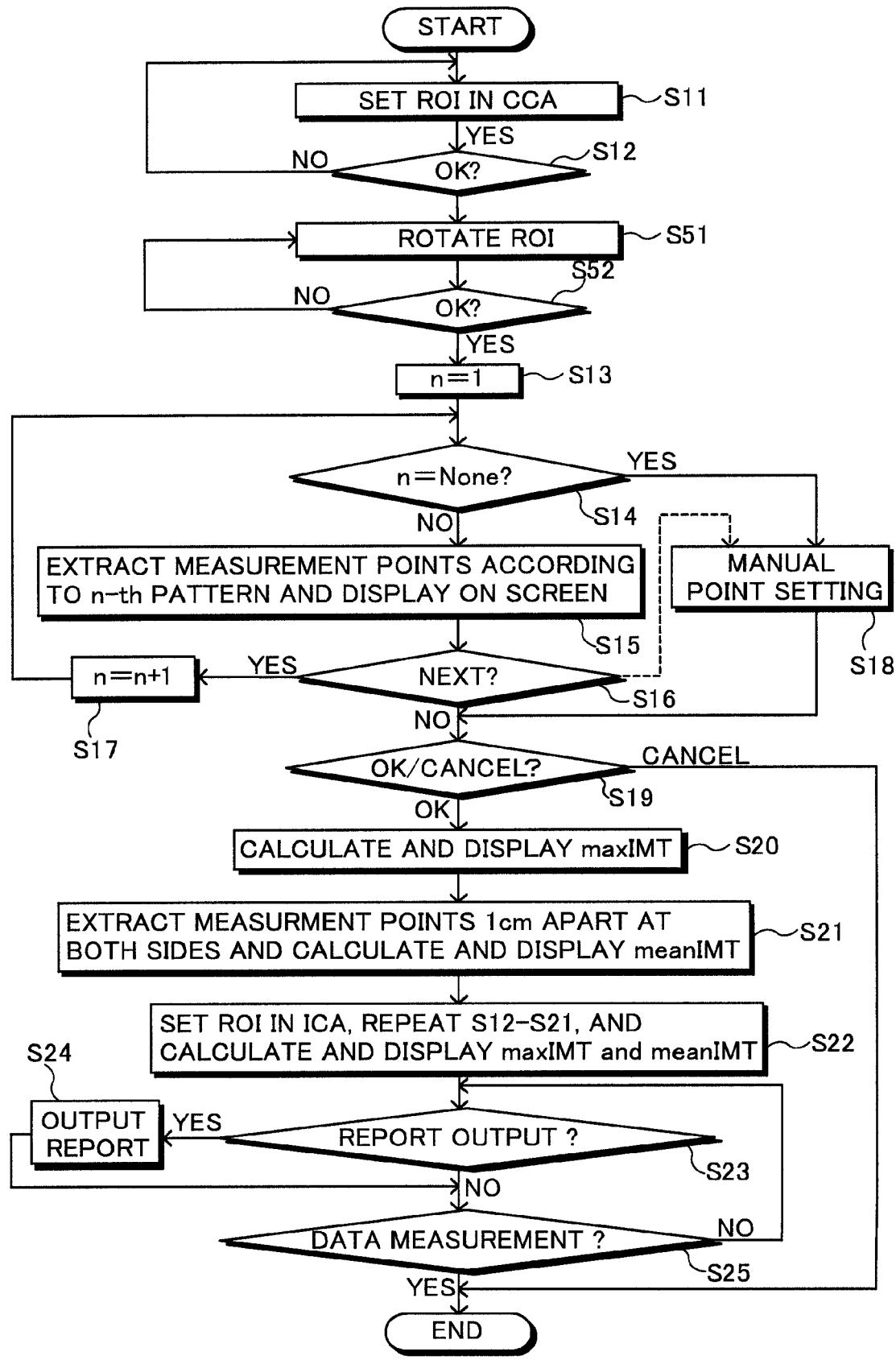

ULTRASONIC DIAGNOSTIC APPARATUS, DATA MEASUREMENT METHOD, AND DATA MEASUREMENT PROGRAM

BACKGROUND OF THE INVENTION

1. Field of the Invention

The present invention relates to an ultrasonic diagnostic apparatus having a function of measuring data such as intima media thickness (IMT) of a blood vessel based on reception signals obtained by transmitting ultrasonic waves to an object to be inspected and receiving ultrasonic waves from the object. Further, the present invention relates to a data measurement method and a data measurement program to be used for the data measurement.

2. Description of a Related Art

Recent years, intima media thickness (IMT) has attracted attention as an indicator for determination of arteriosclerosis. Referring to FIG. 16, an arterial wall has a three-layer structure including an intima 901, a media 902, and an adventitia 903. IMT refers to a thickness of the intima 901 and the media 902 of them (i.e., a length from a boundary between a vascular lumen 900 and the intima 901 to a boundary between the media 902 and the adventitia 903). From recent research, it has been found that the intima media thickness increases and a plaque is formed as arteriosclerosis progresses. Here, the plaque is a part where a vessel wall is raised inwardly. Tissues of the plaque may be various tissues such as blood clot or fatty or fibrous tissues, and cause carotid artery stenosis, cerebral infarction, cerebral ischemia, and so on.

FIGS. 17 and 18 are schematic diagrams showing part of a carotid artery. As shown in FIGS. 17 and 18, the blood pumped from the heart is introduced into a common carotid artery (CCA) 911, and divided into an external carotid artery (ECA) 912 that connects to an artery of the face and an internal carotid artery (ICA) 913 that connects to an artery of the brain.

The above-explained IMT is measured by ultrasonic examination (carotid artery ultrasonic examination). That is, an ultrasonic probe including an ultrasonic transducer array, in which plural ultrasonic transducers are arranged, is brought into contact with the cervical part of an object to be inspected (a patient) to transmit ultrasonic waves. Here, the reason the IMT is measured in the carotid artery is that the carotid artery is a favorite site of arteriosclerosis. In this regard, the plural ultrasonic transducers are sequentially driven and an ultrasonic beam is formed by synchronization of plural ultrasonic waves, and thereby, the object is electronically scanned. Thus transmitted ultrasonic waves are reflected on the surface of a structure within the object (a boundary between different tissues), and resulting ultrasonic echoes are received by the ultrasonic probe and reception signals are generated. These reception signals are processed in an ultrasonic diagnostic apparatus main body connected to the ultrasonic probe, and thereby, an ultrasonic image is generated. Further, an examiner (an operator such as a doctor) measures the vessel wall by using a vernier caliper or the like in the ultrasonic image generated as described above, and therefore, the IMT is obtained. Furthermore, the level of arteriosclerosis is measured based on the IMT and the vessel status throughout the body including the heart and the brain is estimated based on the result.

However, according to the measurement method, there are problems that the measurement requires long time and the measurement accuracy largely varies depending on the levels of skill of examiners. In order to actively utilize IMT in mass checkup or the like, efficient IMT measurement requiring short time and providing measurement results that vary little depending on examiners is desired.

As a related technology, Hiroyuki TOIDE, "PROPER ULTRASONIC EXAMINATION OF BLOOD VESSELS", Ultrasonic examination technique, Vol. 31, No. 2 (2006), pp. 80 discloses precautions and points for ultrasonic examination of blood vessels. In carotid artery ultrasonic examination, the vessel diameter, maxIMT shown in FIG. 17, and mean-IMT shown in FIG. 18 are measured. The meanIMT is obtained by measuring maxIMT and two IMTs at positions "a" and "c" on both sides at 1 cm from it, and calculating an average value of the three points as follows: {maxIMT+IMT(a)+IMT(c)}/3. According to TOIDE, in IMT measurement, measurement is performed in two positions of the common carotid artery 911 and a region from the vascular bifurcation 914 to the internal carotid artery 913. A plaque 915 is likely formed in a region where the direction of blood flow changes like in the vicinity of the entrance of common carotid artery 911 or the vicinity of vascular bifurcation (BIF) 914.

Further, Japanese Patent Publication JP-B-2889568 (Japanese Patent Application Publication JP-A-11-318896) discloses an intima media thickness measurement apparatus including an ultrasonic unit that outputs data of images imaged by using ultrasonic waves as digital data, a data transmission unit that transmits the digital output of the ultrasonic unit by using optical coupling, and a data analysis unit that calculates the intima media thickness of a blood vessel based on the image data of the blood vessel transmitted by the data transmission unit, and the data analysis unit calculates a reference position based on a moving average value of intensity values of the digital image data and calculates the intima media thickness of the blood vessel based on the local maximum value and the local minimum value of the intensity values within a predetermined pixel range from the reference position toward the vessel wall of the blood vessel.

In JP-B-2889568, the IMT value is automatically calculated by searching for peak values of intensity. However, which points (local maximum points or local minimum points) are used in IMT measurement depends on examiners' criteria and preferences. Further, it is not always to obtain desired results by using the same points at every time because the statuses and conditions of ultrasonic images are not necessarily the same at every time in view of the influence of noise. Furthermore, in JP-B-2889568, the operation in the case where no desired measurement result is obtained (e.g., recurrent computation) is complex, and therefore, efficient examinations can hardly be performed in medical checkups or the like. Moreover, no method of calculating maxIMT or mean IMT is mentioned in JP-B-2889568.

Japanese Patent Application Publication JP-P2005-118314A discloses an ultrasonic diagnostic apparatus including an ultrasonic probe that transmits ultrasonic waves into a body of an object to be inspected and receiving the ultrasonic waves reflected within the body to convert them into high-frequency electric signals, A/D converting means for converting the high-frequency electric signals into high-frequency digital data, high-frequency digital data storing means for storing the high-frequency digital data, image data converting means for converting the high-frequency digital data into digital data for image display, image display means for displaying images based on the data for image display, and data analysis means for acquiring the high-frequency digital data from the high-frequency digital data storing means and performing a predetermined analysis thereon. The data analysis means detects inner walls of intima and adventitia of a blood vessel and calculates intima media thickness.

In JP-P2005-118314A, RF data is stored in the CINE memory and predetermined data processing (e.g., filtering processing for removing noise) is performed on image data that has been converted from the RF data, and IMT is automatically calculated based on the image data after data processing (paragraphs 0022, 0026, 0027). Then, if no desired calculation result is obtained, the parameters for data processing such as filtering processing is reset and calculation for obtaining IMT is performed again (paragraph 0030). However, since the RF data is large in data amount, the cost of the CINE memory becomes high. Further, since resetting of parameters must be done by the examiner, the efficient examinations can hardly be performed in medical checkups or the like and variations in results may be caused depending on examiners.

SUMMARY OF THE INVENTION

The present invention has been achieved in view of the above-mentioned problems. A purpose of the present invention is to provide an ultrasonic diagnostic apparatus by which data measurement such as IMT examination can be efficiently performed by a simple operation. A further purpose of the present invention is to provide a data measurement method and a data measurement program to be used for the data measurement in the ultrasonic diagnostic apparatus.

In order to accomplish the above-mentioned purposes, an ultrasonic diagnostic apparatus according to one aspect of the present invention includes: an ultrasonic probe for transmitting ultrasonic waves to an object to be inspected and receiving ultrasonic echoes generated by reflection of the ultrasonic waves in the object to output reception signals; signal processing means for performing at least envelope detection processing on the reception signals outputted from the ultrasonic probe to generate envelope data; image data generating means for generating image data representing an ultrasonic image on the object based on the envelope data; pre-measurement processing means for performing structural image generating processing on the envelope data; and measuring means for performing measurement based on the envelope data processed by the pre-measurement processing means.

Further, a data measurement method according to one aspect of the present invention is a method to be used in an ultrasonic diagnostic apparatus for transmitting ultrasonic waves to an object to be inspected and receiving ultrasonic echoes generated by reflection of the ultrasonic waves in the object to obtain reception signals and performing at least envelope detection processing on the reception signals to generate the envelope data, and the method includes the steps of: (a) generating image data representing an ultrasonic image on the object based on the envelope data; (b) performing structural image generating processing on the envelope data; and (c) performing measurement based on the envelope data processed at step (b).

Furthermore, a data measurement program according to one aspect of the present invention is a program embodied on a computer readable medium, to be used in an ultrasonic diagnostic apparatus for transmitting ultrasonic waves to an object to be inspected and receiving ultrasonic echoes generated by reflection of the ultrasonic waves in the object to obtain reception signals and performing at least envelope detection processing on the reception signals to generate envelope data, and the program actuates a CPU to execute the procedures of: (a) generating image data representing an ultrasonic image on the object based on the envelope data; (b) performing structural image generating processing on the envelope data; and (c) performing measurement based on the envelope data processed at procedure (b).

According to the present invention, since measurement is performed after structural image generating processing has been performed on the envelope data, data measurement such as IMT examination can be efficiently performed by a simple operation.

BRIEF DESCRIPTION OF THE DRAWINGS

FIG. 14 is a flowchart showing an IMT measurement operation in the ultrasonic diagnostic apparatus according to the third embodiment of the present invention;

DESCRIPTION OF THE PREFERRED EMBODIMENTS

Hereinafter, preferred embodiments of the present invention will be explained in detail with reference to the drawings. The same reference numbers are assigned to the same component elements and the description thereof will be omitted.

Figure 1:
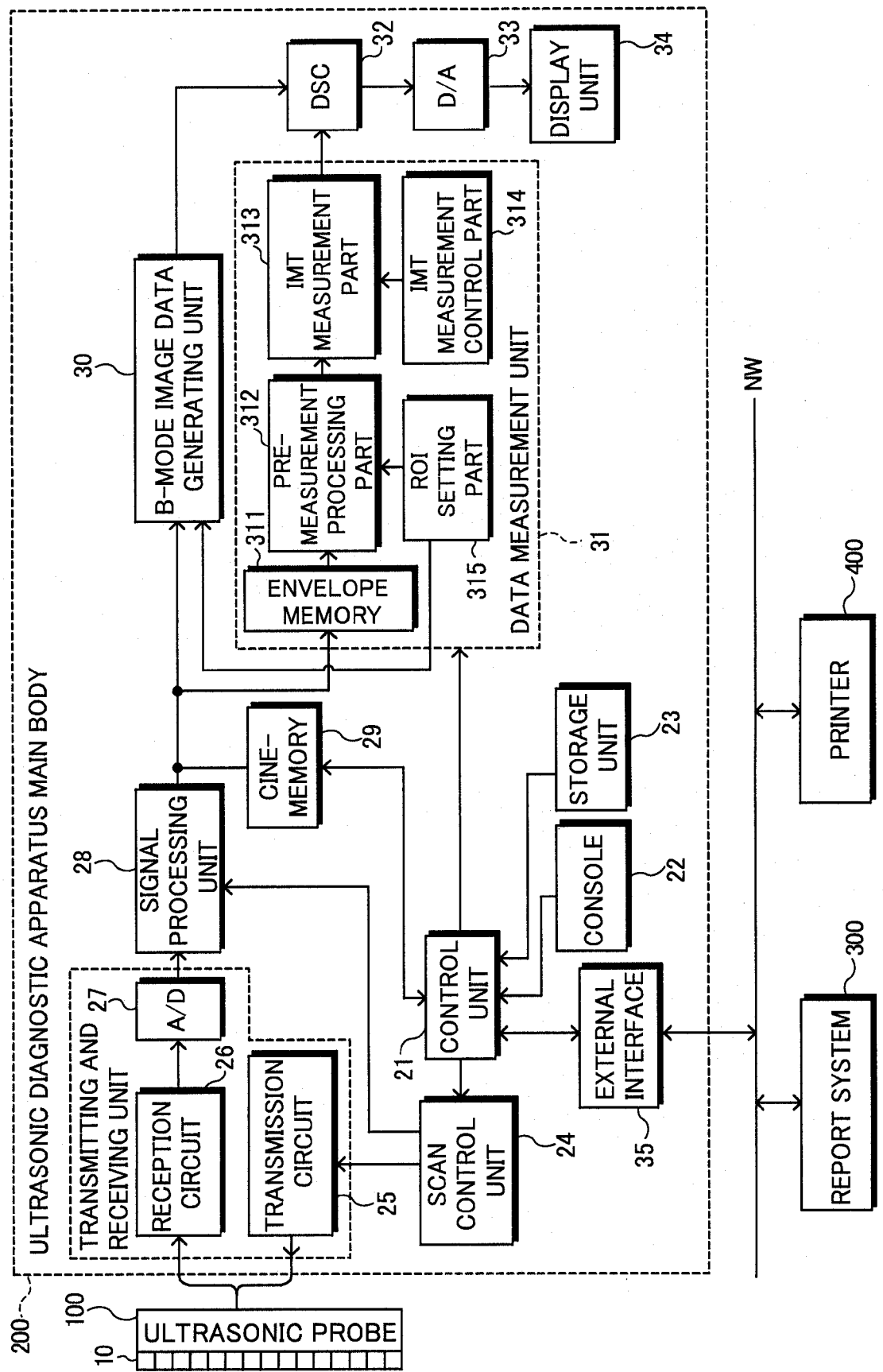
FIG. 1 is a block diagram showing a configuration of an ultrasonic diagnostic apparatus according to the first embodiment of the present invention.

FIG. 1 is a block diagram showing an ultrasonic diagnostic apparatus according to the first embodiment of the present invention. The ultrasonic diagnostic apparatus includes an ultrasonic probe 100 that transmits and receives ultrasonic waves, and an ultrasonic diagnostic apparatus main body 200 that controls transmission and reception of ultrasonic waves to generate an ultrasonic image based on acquired reception signals. Further, the ultrasonic diagnostic apparatus main body 200 has an intima media thickness (IMT) measurement function of an artery, a circulatory measurement function, and an obstetric measurement function. The ultrasonic probe 100 and the ultrasonic diagnostic apparatus main body 200 are connected to each other via a cable. Further, such an ultrasonic diagnostic apparatus may be connected to a report system 300 or printer 400 via a network NW such as a LAN.

The ultrasonic probe 100 is a probe of convex type, linear scan type, or sector scan type and used in contact with an object to be inspected. The ultrasonic probe 100 includes plural ultrasonic transducers 10 that form one-dimensional or two-dimensional transducer array. The ultrasonic transducers 10 transmit an ultrasonic beam to the object according to applied drive signals, and receive ultrasonic echoes reflected from the object to output reception signals.

Each ultrasonic transducer is constructed of a vibrator in which electrodes are formed on both ends of a material having a piezoelectric property (piezoelectric material) such as a piezoelectric ceramic represented by PZT (Pb (lead) zirconate titanate), a polymeric piezoelectric element represented by PVDF (polyvinylidene difluoride), or the like. When a voltage of a pulsed or continuous wave electric signal is applied to the electrodes of the vibrator, the piezoelectric material expands and contracts. By the expansion and contraction, pulsed or continuous wave ultrasonic waves are generated from the respective vibrators, and an ultrasonic beam is formed by synthesizing these ultrasonic waves. Further, the respective vibrators expand and contract by receiving propagating ultrasonic waves to generate electric signals. These electric signals are outputted as reception signals of the ultrasonic waves.

Alternatively, as the ultrasonic transducers, plural kinds of elements of different ultrasonic conversion types may be used. For example, the above-mentioned vibrators are used as elements for transmitting ultrasonic waves and photo-detection type ultrasonic transducers are used as elements for receiving ultrasonic waves. The photo-detection type ultrasonic transducer is for detecting ultrasonic signals by converting the ultrasonic signals into optical signals, and constituted from a Fabry-Perot resonator or fiber Bragg grating, for example.

The ultrasonic diagnostic apparatus main body 200 includes a control unit 21 that controls operation of the entire ultrasonic diagnostic apparatus, a console 22, a storage unit 23, a scan control unit 24, a transmitting and receiving unit including a transmission circuit 25, a reception circuit 26, and an A/D converter 27, a signal processing unit 28, a cine-memory 29, a B-mode image data generating unit 30, a data measurement unit 31, a DSC (digital scan converter) 32, a D/A converter 33, a display unit 34, and an external interface 35.

Figure 2:
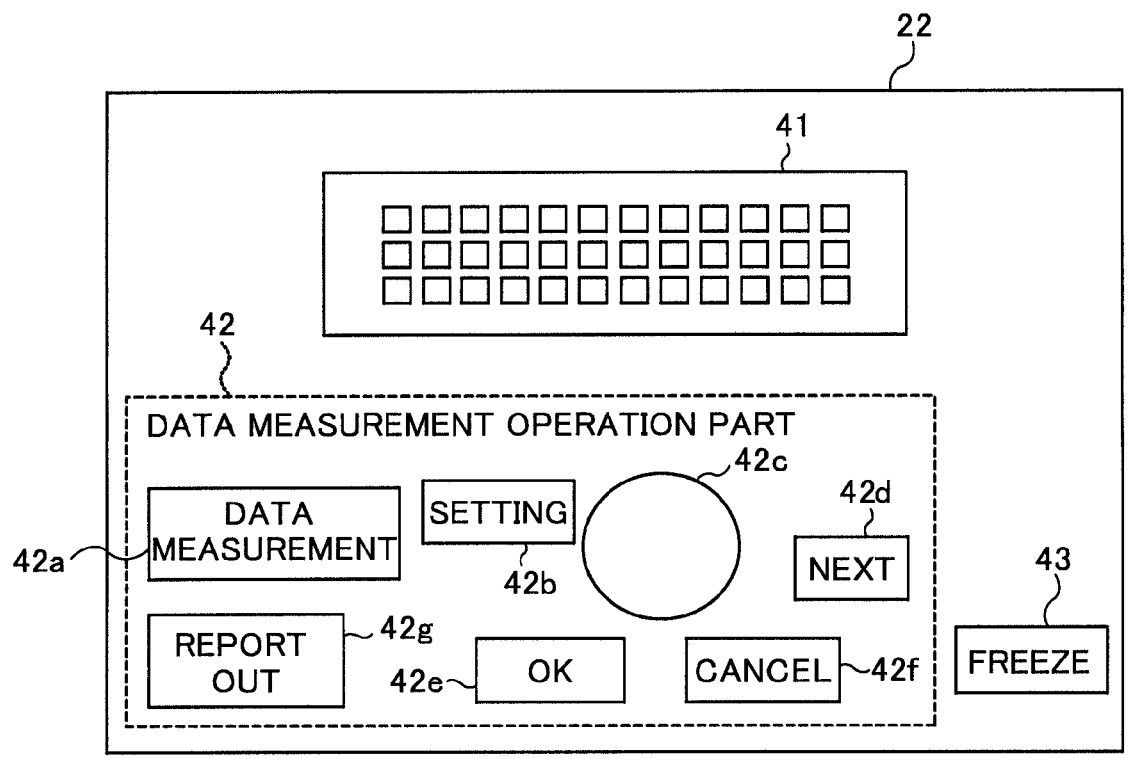
FIG. 2 is a schematic diagram showing a configuration of a console shown in FIG. 1.

The console 22 is an input device to be used by an examiner (operator) when various commands and information are inputted to the ultrasonic diagnostic apparatus main body 200. As shown in FIG. 2, the console 22 is provided with character input keys 41, a data measurement operation part 42, and a freeze button 43. The character input keys 41 are used when patient information is inputted, for example. Further, the data measurement operation part 42 is used when various data on ultrasonic images such as IMT are measured, and includes a data measurement button 42a, a setting button 42b, a track ball 42c, a next button 42d, an OK button 42e, a cancel button 42f, a report output button 42g, and so on. Furthermore, the freeze button 43 is provided for switching between the live mode (moving image) and freeze mode (still image) with respect to the ultrasonic image being displayed on the screen, and at each time when the freeze button 43 is pushed down, a freeze signal and a freeze release signal are alternately inputted to the control unit 21 (FIG. 1).

The storage unit 23 is constituted of a hard disk, memory, or the like, and stores programs (software) for actuating a CPU included in the ultrasonic diagnostic apparatus main body 200 to execute operations including various kinds of processing, information to be used for the processing, and so on.

The scan control unit 24 sequentially sets transmission directions of ultrasonic beams or reception directions of ultrasonic echoes under the control of the control unit 21, and has a transmission control function of selecting transmission delay patterns according to the set transmission directions and a reception control function of selecting reception delay patterns according to the set reception directions.

Here, the transmission delay pattern refers to a pattern of delay time to be provided to the drive signals for forming an ultrasonic beam in a desired direction with the ultrasonic waves transmitted from the plural ultrasonic transducers 10, and the reception delay pattern refers to a pattern of delay time to be provided to the reception signals for extracting ultrasonic echoes from a desired direction with the ultrasonic waves received by the plural ultrasonic transducers. Plural transmission delay patterns and plural reception delay patterns are stored in a memory or the like.

The transmission circuit 25 generates drive signals to be respectively applied to the plural ultrasonic transducers 10. At that time, the transmission circuit 25 can provide respective delay times to the drive signals based on the transmission delay pattern selected by the scan control unit 24. Here, the transmission circuit 25 may adjust the amounts of delay of the drive signals and supply the drive signals to the ultrasonic probe 100 such that the ultrasonic waves to be transmitted from the plural ultrasonic transducers 10 form an ultrasonic beam, or may supply drive signals to the ultrasonic probe 100 such that the ultrasonic waves to be transmitted at once from the plural ultrasonic transducers 10 reach the entire imaging region of the object.

The reception circuit 26 amplifies the reception signals respectively outputted from the plural ultrasonic transducers 10, and the A/D converter 27 converts the analog reception signals amplified by the reception circuit 26 into digital reception signals (also referred to as "RF data" in this application). The RF data outputted from the A/D converter 27 is inputted to the signal processing unit 28. The signal processing unit 28 performs reception focus processing by providing the respective delay times to the reception signals represented by the RF data based on the reception delay pattern selected by the scan control unit 24, and adding those reception signals to one another. Through the reception focus processing, sound ray data is formed, in which the focal point of the ultrasonic echoes is narrowed.

Furthermore, the signal processing unit 28 corrects attenuation of the sound ray data by distance according to the depths of the reflection positions of ultrasonic waves through STC (sensitivity time gain control), and then, performs envelope detection processing with a low-pass filter or the like thereon to generate envelope data.

The envelope data generated by the signal processing unit 28 are sequentially stored in the cine-memory 29 and supplied to the B-mode image data generating unit 30. The cine-memory 29 has a memory capacity for storing envelope data for plural frames. The B-mode image data generating unit 30 performs pre-process processing such as Log (logarithmic) compression and gain adjustment on the envelope data to generate B-mode image data, and outputs the generated B-mode image data to the DSC 32. The processing such as Log (logarithmic) compression may be performed in the signal processing unit 28.

The data measurement unit 31 has an envelope memory 311, a pre-measurement processing part 312, an IMT measurement part 313, an IMT measurement control part 314, and an ROI setting part 315, and measures IMT based on the envelope data.

In the embodiment, the data measurement unit 31 except for the envelope memory 311 is constituted from a central processing unit (CPU) and software for actuating the CPU to perform various kinds of processing. However, they may be constituted from digital circuits or analog circuits. Further, the control unit 21, the scan control unit 24, the signal processing unit 28, the B-mode image data generating unit 30, and the DSC 32 are also constituted from a CPU and software. However, the signal processing unit 28, the B-mode image data generating unit 30, and the DSC 32 may be constituted from digital circuits or analog circuits. The above-mentioned software is stored in the storage unit 23. Further, the transmission delay patterns and reception delay patterns to be selected by the scan control unit 24 may be stored in the storage unit 23.

The DSC 32 converts (raster-converts) the B-mode image data generated by the B-mode image data generating unit 30 into ultrasonic image data that follows the normal scan system of television signals, and performs necessary image processing such as gradation processing to generate ultrasonic image data. Further, the DSC 32 generates image data for display based on the ultrasonic image data. Furthermore, the DSC 32 generates synthesized data for color presentation of intima media in an ultrasonic image and superimposes display of various information on the ultrasonic image based on the data outputted from the data measurement unit 31. An image processing part for performing image processing such as linear gradation processing including gain adjustment and contrast adjustment and nonlinear gradation processing including γ-correction may be provided at the downstream of the DSC 32.

The D/A converter 33 converts the image data for display converted in the DSC 32 into analog signals and outputs the analog signals to the display unit 34.

The display unit 34 is a raster-scan type CRT display or LCD display, and displays moving images or still images of ultrasonic images, various setting screens, IMT measurement results, and so on based on the image signals analog-converted in the D/A converter 33. Although one display unit is provided in the embodiment, another display unit may be provided for display of the various setting screens, for example.

Next, a function of the data measurement unit 31 in the ultrasonic diagnostic apparatus shown in FIG. 1 will be explained.

The envelope memory 311 stores envelope data supplied from the signal processing unit 28 in the live mode and stores envelope data supplied from the cine-memory 29 in the freeze mode.

The pre-measurement processing part 312 reads out the envelope data corresponding to a region of interest set by the ROI setting part 315 from the envelope memory 311, and performs image processing such as smoothing processing, contrast enhancement processing, edge enhancement processing, noise reduction processing, or structural image generating processing. Thereby, envelope data more suitable for IMT measurement processing (more easily measurable) is obtained. Here, a structural image refers to an image obtained by subtracting a speckle image from an ultrasonic image. In the structural image, information on edges, boundary lines, and soon are saved, and the image is effective for IMT measurement. Especially, even when a boundary of intima or media is partly disconnected in a normal B-mode image, IMT measurement can be performed by generating a structural image.

Here, the generating processing of structural image will be explained in detail.

First, local maximum points and local minimum points of a signal represented by envelope data are obtained. The local maximum points and local minimum points can be obtained by calculating first derivative and second derivative of the signal representing the envelope data. In this case, rather than adopting the local maximum points and local minimum points that have been simply obtained based on differential calculation, it is desirable to add a condition that a distance from the local maximum point or local minimum point obtained immediately before is calculated, and if the distance is longer than the wavelength of ultrasonic waves transmitted, the point is not adopted or the like. This is because local maximum/minimum points caused by speckles and local maximum/minimum points caused by structures may be mixed in the envelope data.

Then, a signal representing an average value of a signal representing the local maximum point and a signal representing the local minimum point obtained as described above are obtained. The signal representing the average value corresponds to structural image data representing an ultrasonic image of a structure, that is, a structural image in an imaging region. The reason why the local maximum points and the local minimum points in envelop data are used rather than typical filter processing in order to obtain a signal representing a structure is as follows. That is, the size of a speckle pattern (speckle size) emerging in an imagine region differs depending on the depth of the imaging region, and thus, if filter processing is equally performed on envelope data, speckles may not be removed, or contrary, also signals representing structures may be removed.

The IMT measurement part 313 obtains IMT by searching for plural measurement points on the preprocessed envelope data, and calculates the maximum value of IMT (maxIMT) and a mean value (meanIMT) in three points of maxIMT and at both sides at 1 cm from it.

The IMT measurement control part 314 sets a combination pattern of plural measurement points to be used in an IMT measurement processing unit 37 according to operator's operation. Here, plural combination patterns of plural measurement points have been prepared in advance in the IMT measurement control part 314, and the IMT measurement control part 314 sequentially apply those combination patterns to the IMT measurement part 313 according to user setting. A memory for storing the plural combination patterns may be separately prepared.

The ROI setting part 315 displays ROI on the B-mode image according to the examiner's operation, and gives instruction on a range of envelope data to be preprocessed (envelope data corresponding to the region of interest) to the pre-measurement processing part 312.

Next, the setting operation of measurement points that is performed prior to IMT measurement in the ultrasonic diagnostic apparatus according to the embodiment will be explained.

Figure 3:
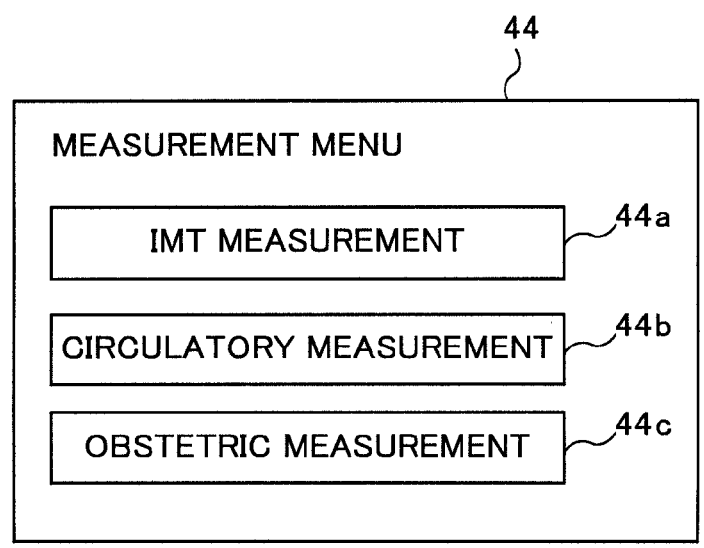
FIG. 3 is a schematic diagram showing a measurement menu screen.

When IMT measurement is performed, an examiner first pushes down the data measurement button 42a shown in FIG. 2. Thereby, a measurement menu screen 44 shown in FIG. 3 is displayed on the display unit 34. The examiner selects an IMT measurement button 44a and pushes down the setting button 42b (FIG. 2) on the measurement menu screen 44. Thereby, the ultrasonic diagnostic apparatus enters the IMT measurement mode, and the envelope data signal-processed in the signal processing unit 28 are sequentially inputted or the envelope data stored in the cine-memory 29 are inputted for each frame to the envelope memory 311. Other measurements may be performed in the ultrasonic diagnostic apparatus according to the embodiment, and, in that case, the examiner selects a desired button such as a circulatory measurement button 44b or an obstetric measurement button 44c.

Figure 4:
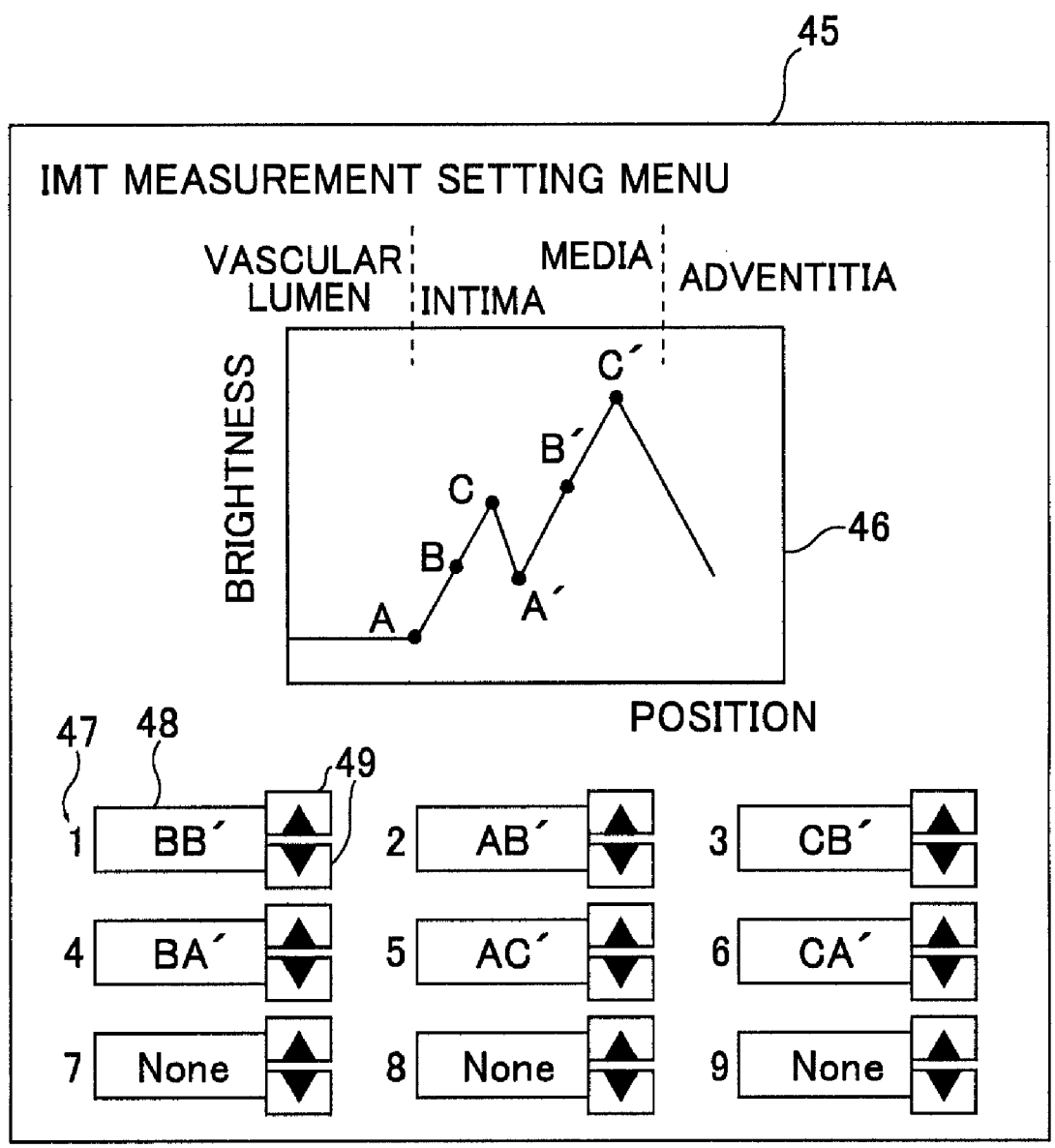
FIG. 4 is a schematic diagram showing an IMT measurement setting menu screen.

When the setting button 42b shown in FIG. 2 is pushed down in the IMT measurement mode, an IMT measurement setting menu screen 45 shown in FIG. 4 is displayed on the display unit 34. The examiner sets the order of priority of plural measurements to be used when IMT is calculated in the screen.

As shown in FIG. 4, the IMT measurement setting menu screen 45 includes a measurement point display area 46, priority display parts 47, measurement point selection columns 48, and scroll buttons 49. In the measurement point display area 46, there is shown a graph representing reflection intensity (brightness) when ultrasonic waves are reflected by an artery wall based on the envelope data stored in the envelope memory 311.

Since the ultrasonic waves are strongly reflected at a boundary between a vascular lumen and an intima and a boundary between a media and an adventitia, two peaks primarily appear in values of the envelope data obtained by transmission and reception of ultrasonic waves as shown in the measurement point display area 46. IMT is a distance between those two boundaries, and various combination patterns such as local minimum point A and local minimum point A', local maximum point C and local maximum point C', midpoints B and B' between the local maximum points and the local minimum points, and local minimum point A and local maximum point C' may be used as measurement points.

Accordingly, the examiner selects plural combination patterns of two positions to be used as measurement points for the two peaks with their priorities. Specifically, by operating the scroll buttons 49, desired combination patterns (BB', AB', . . . ) of measurement points (A-C, A'-C') are displayed in the measurement point selection columns 48 in the order of descending priorities (refer to priority display parts 47). Which positions are used as measurement points depends on examiners' criteria and preferences, and a specific measurement point (e.g., the local minimum point) is difficult to be extracted depending on the condition of ultrasonic image (e.g., influence of noise or the like). Therefore, plural combination patterns are selected so that, if appropriate measurement points are impossible to be extracted according to one combination pattern, another combination pattern is used for extraction. In FIG. 4, the combination patterns from the first priority to the sixth priority are set.

When the setting of the combination patterns of measurement points is ended and the setting button 42b is pushed down again, the IMT measurement setting menu screen 45 is cancelled. If the priorities have been set in advance and there is no need to change the priorities, resetting may not be required.

Figure 5:
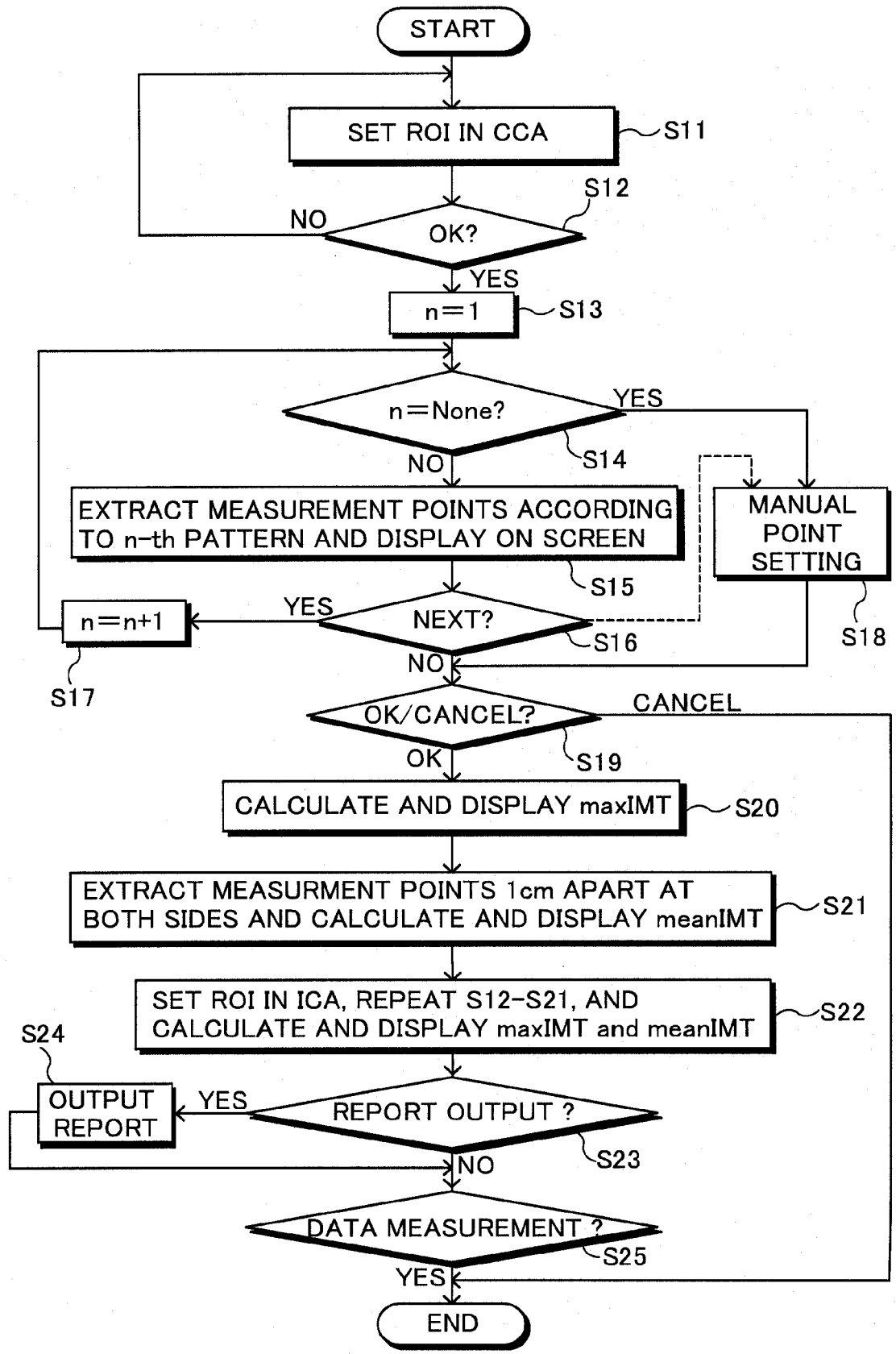
FIG. 5 is a flowchart showing an IMT measurement operation in the ultrasonic diagnostic apparatus according to the first embodiment of the present invention.
Figure 6:
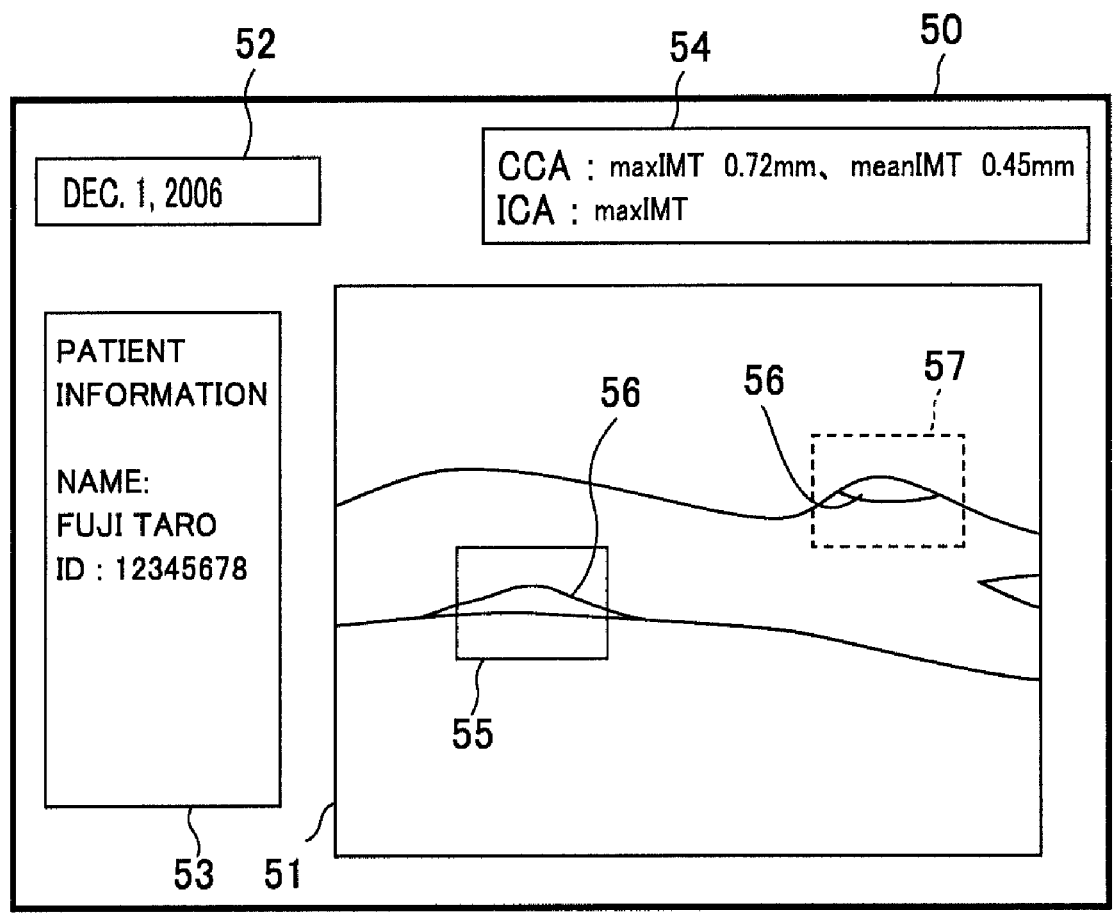
FIG. 6 is a schematic diagram showing an IMT examination screen.

Next, an IMT measurement operation in the ultrasonic diagnostic apparatus according to the embodiment will be explained. FIG. 5 is a flowchart showing the IMT measurement operation. Further, FIG. 6 shows an IMT examination screen 50 displayed on the display unit 34. The IMT examination screen 50 includes an ultrasonic image (B-mode image) display area 51, an examination date display column 52, a patient information display column 53, and a measurement result display column 54.

Ultrasonic imaging is started when the examiner brings the ultrasonic probe 100 (FIG. 1) in contact with the cervical part of a patient, and then, a B-mode image is displayed in the ultrasonic image display area 51. In the case where diagnosis of arterial sclerosis or the like is made by IMT measurement, maxIMT and meanIMT are measured in each of a common carotid artery (CCA) and an internal carotid artery (ICA).

First, at step S11 in FIG. 5, the examiner sets an ROI 55 in CCA by using the track ball 42c (FIG. 2) while observing an ultrasonic image (see FIG. 6) displayed on the display unit. In this regard, the examiner selects a region considered to be a plaque 56 or a region where the vessel wall is thick. In response, the ROI setting part 315 (FIG. 1) allows the B-mode image data generating unit 30 to display the selected region on the B-mode image being displayed. The examiner determines ROI by pushing down the OK button 42e if the selected region is appropriate. On the other hand, the examiner selects another region by pushing down the cancel button 42f if the selected region is not appropriate (step S12). When ROI is determined, the ROI setting part 315 designates a data region corresponding to the ROI 55 from among the envelope data stored in the envelope memory 311 for the pre-measurement processing part 312. In response, the pre-measurement processing part 312 performs pre-processing on the envelope data included in the data region and outputs the envelope data to the IMT measurement part 313.

At step S13, the IMT measurement control part 314 applies a combination pattern having the first number of priority "n" from among preset combination patterns of measurement points to the IMT measurement part 313. Since n=1 (n≠None) at step S14, the processing moves to step S15. At step S15, the IMT measurement part 313 extracts measurement points to be used for IMT measurement according to the preprocessed envelope data and the combination pattern of measurement points having currently applied priority "n", and displays them on the B-mode image.

Here, an extraction algorithm of measurement points at step S15 will be explained with reference to FIGS. 7A-8.

Figure 7A:
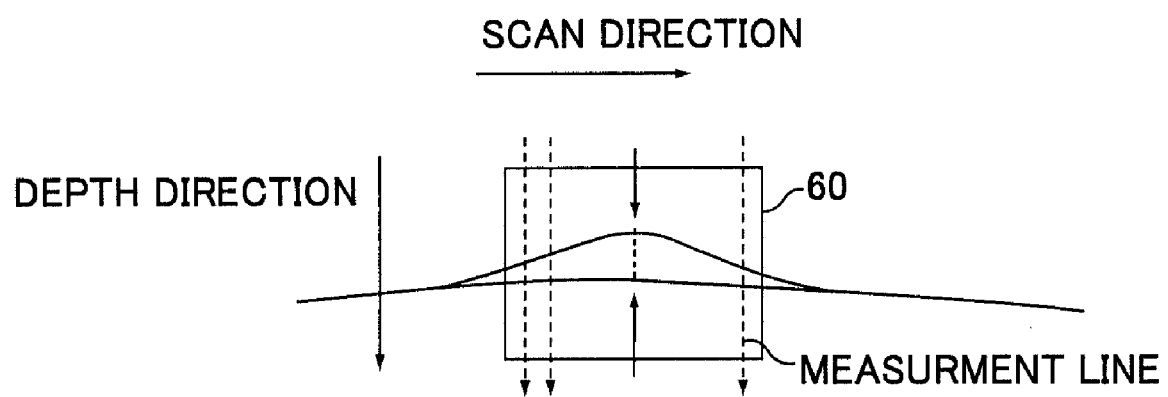
FIGS. 7A and 7B are diagrams for explanation of an algorithm for extraction of measurement points.
Figure 8:
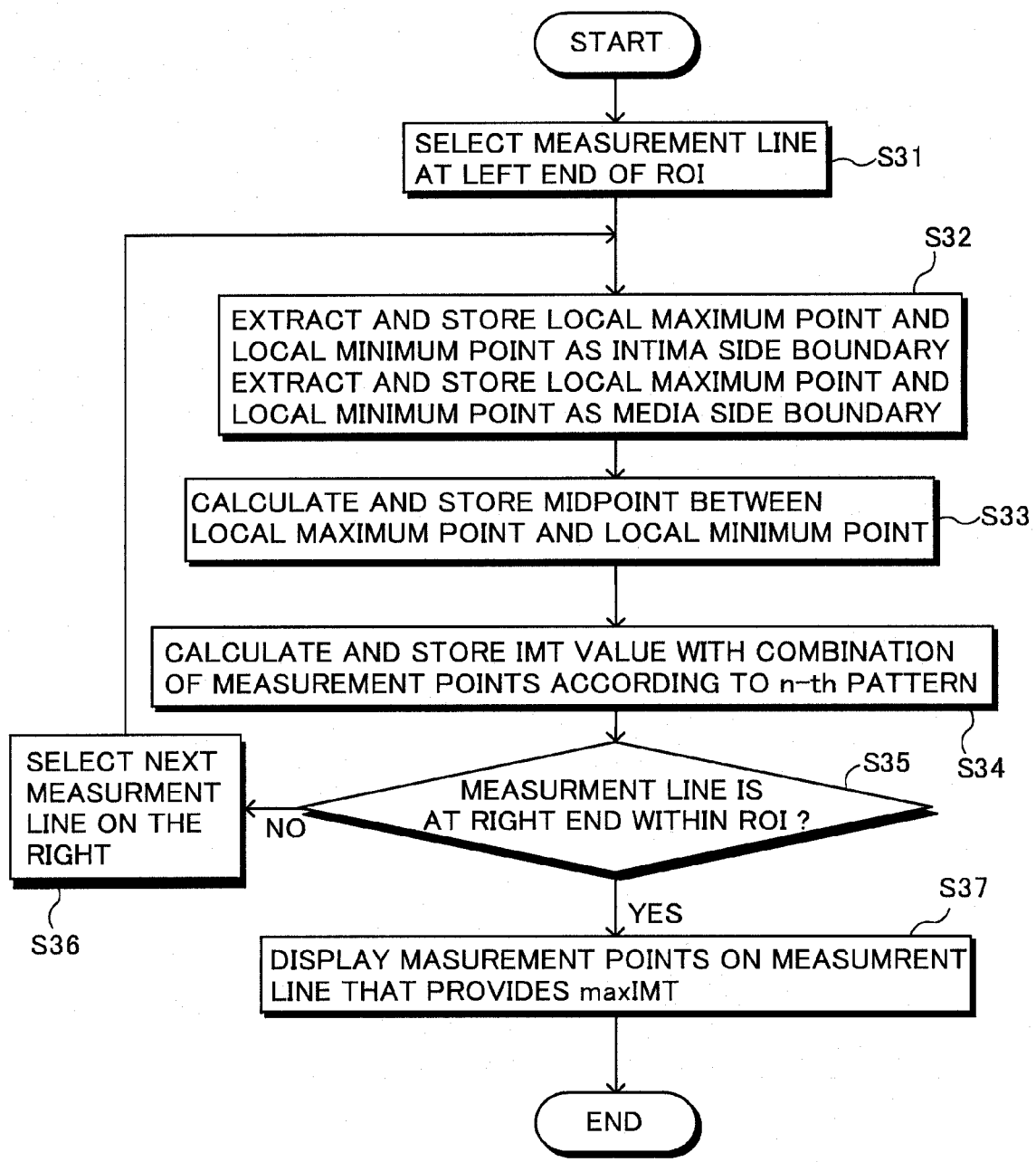
FIG. 8 is a flowchart showing the algorithm for extraction of measurement points.

As shown in FIG. 7A, one pair of sides (in the horizontal direction of the drawing) of a frame (rectangle) showing ROI 60 are set along the scan direction (azimuth direction) of ultrasonic waves, and the other pair of sides (in the vertical direction of the drawing) are set along the depth direction. In the embodiment, IMT is measured in the depth direction.

Figure 7B:
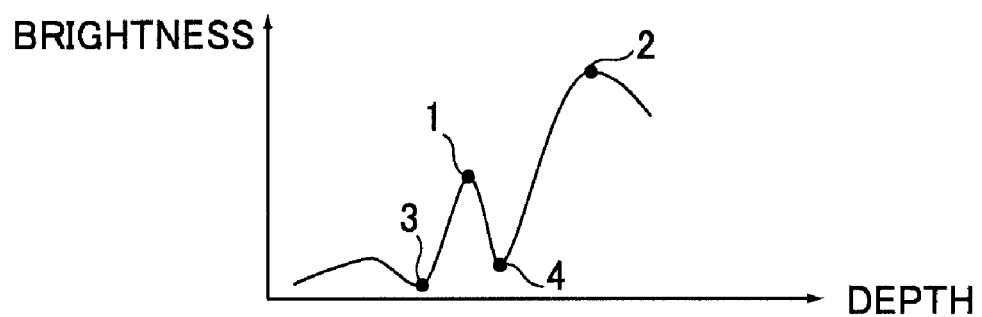

As shown in FIG. 7B, typically, two peaks representing a boundary between a vascular lumen and an intima (hereinafter, also referred to as an intima side boundary of IMT) and a boundary between a media and an adventitia (hereinafter, also referred to as a media side boundary of IMT) appear in a profile of measurement lines within the ROI 60. Accordingly, at step S31 in FIG. 8, the IMT measurement part 313 selects the measurement line at the left end within the ROI 60. Then, at step S32, local maximum point 1 and local minimum point 3 nearest in the shallower direction are extracted as an intima side boundary of IMT and their position coordinates (depths) are stored. On the other hand, local maximum point 2 and local minimum point 4 nearest in the shallower direction are extracted as a media side boundary of IMT and their position coordinates (depths) are stored. Then, at step S33, the IMT measurement part 313 calculates position coordinates of the midpoint between the local maximum point 1 and the local minimum point 3 at the intima side and the midpoint between the local maximum point 2 and the local minimum point 4 at the media side and stores them.

Then, at step S34, the IMT measurement part 313 calculates IMT according to the currently set combination pattern of measurement points having priority "n" and stores it. For example, as shown in FIG. 4, when BB' (midpoint-midpoint) having the first priority is set as the combination pattern of measurement points, the position coordinates of the midpoint B are subtracted from the position coordinates of the midpoint B', and the obtained value is used as IMT. The IMT measurement part 313 repeats such IMT calculation operation while shifting the measurement line within the ROI 60 shown in FIG. 7A to the right until the measurement line reaches the right end within the ROI 60 (steps S35 and S36). The interval between the shifted measurement lines is desirably made equal to the scan interval of ultrasonic beams.

When finished to calculate IMTs with respect to all measurement lines within the ROI 60, at step S37, the IMT measurement part 313 compares the calculated IMTs and extracts the measurement line that provides the maximum IMT (maxIMT). Further, the IMT measurement part 313 outputs measurement points (extracted points) on the extracted measurement line and displays them in corresponding positions on the B-mode image being displayed on the display unit 34.

Referring to FIG. 5 again, when the examiner judges that the extracted measurement points are inappropriate by referring to the B-mode image being displayed, the examiner pushes down the NEXT button 42d. In response, the IMT measurement control part 314 applies a combination pattern having the second priority (n+1=2) from among the preset combination patterns of measurement points to the IMT measurement part 313 (step S17), and extracts measurement points in ROI again.

Such measurement point extraction on ROI is performed until the examiner pushes down the OK button 42e (step S19) or all combination patterns of measurement points that have been preset in the IMT measurement setting menu screen 45 (FIG. 4) are used up (up to n=6 in FIG. 4). Then, if no desired measurement points are obtained according to the final combination pattern, that is, if n=None at step S14, manual point setting is performed by the examiner (step S18). In this case, the examiner sets measurement points by moving the cursor position on the ultrasonic image and selecting desired two points while operating the trackball 42c and the OK button 42e.

Alternatively, if the examiner judges that the automatic extraction of appropriate measurement points is difficult from the ultrasonic image, the examiner may exit from the automatic extraction mode and manually set measurement points (steps S16 and S18). In this case, even if the combination patterns of measurement points that have preset but not yet been used are left, the examiner may enter the manual setting mode by pressing the NEXT button 42d.

At step S19, when the examiner uses the automatically extracted measurement points or the manually set measurement points, the examiner pushes down the OK button 42e. On the other hand, when the examiner judges that it is impossible to extract appropriate measurement points, the examiner pushes down the cancel button 42f. In the latter case, the IMT measurement mode ends.

At step S20, the IMT measurement part 313 measures maxIMT within the ROI based on the automatically extracted measurement points and outputs it. Thereby, the value of maxIMT in CCA is displayed in the measurement result display column 54 shown in FIG. 6. Further, at step S21, the IMT measurement part 313 extracts IMTs at points 1 cm apart at both sides of the maxIMT, and calculates the mean value meanIMT of the IMTs at the three points and outputs it. Thereby, the value of meanIMT in CCA is displayed in the measurement result display column 54 shown in FIG. 6.

Then, at step S22, the IMT measurement part 313 and the IMT measurement control part 314 set ROI 57 (FIG. 6) in ICA and measures IMTs there, and thereby, obtains maxIMT and mean IMT. The details of the steps are the same as those at steps S12-S21.

Then, at step S23, the examiner pushes down the report output button 42g (FIG. 2), and, at step S24, the control unit 21 outputs IMT measurement results to the report system 300, printer 400, or the like connected via the network NW.

Figure 9:
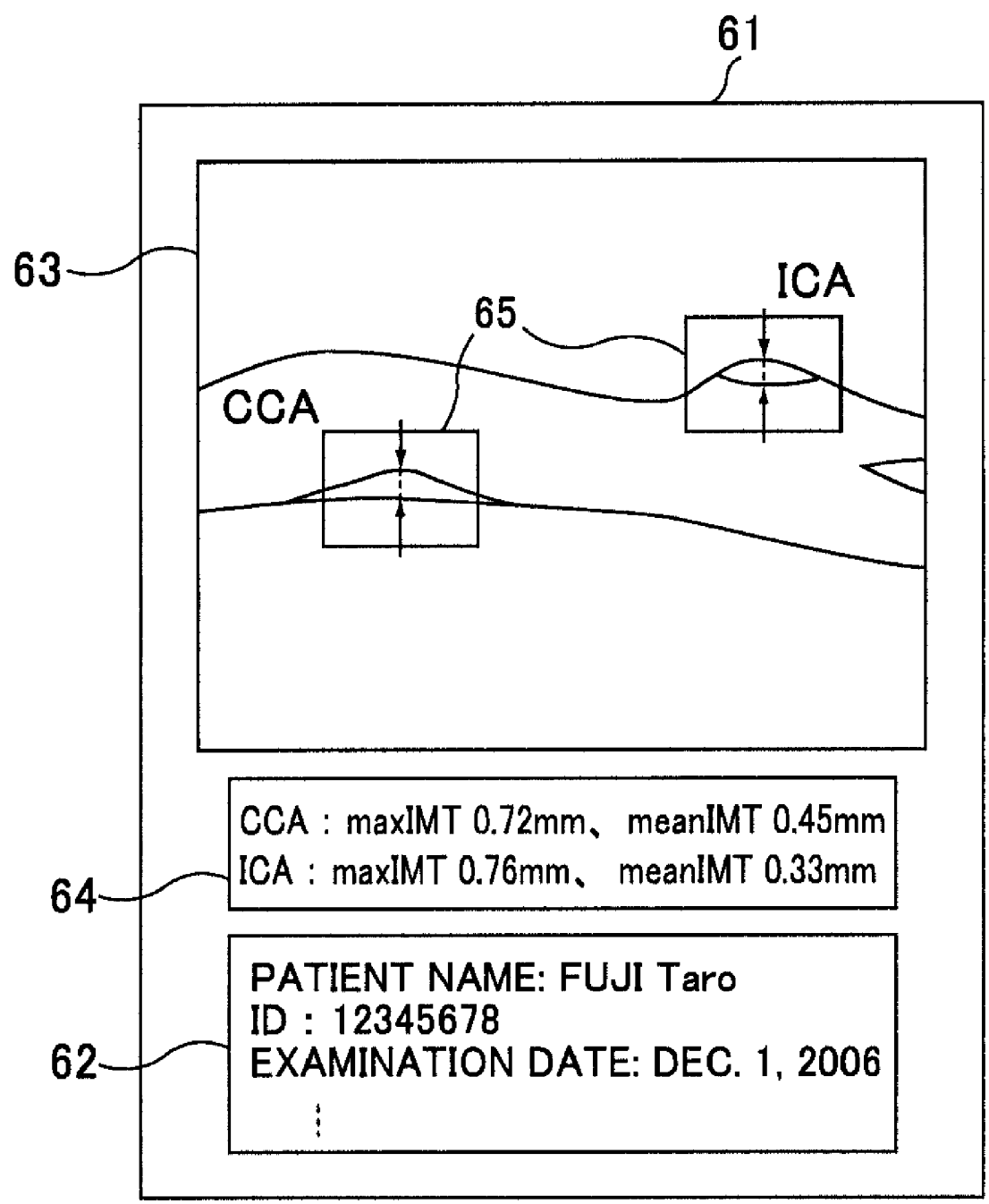
FIG. 9 is a schematic diagram showing an output result screen of an IMT measurement report.

FIG. 9 shows a report output screen 61 to be outputted to the report system 300 or the like. This screen 61 includes an examination information display column 62 including patient information, examination date information, and so on, an ultrasonic image (B-mode image) display area 63, and a measurement result display column 64. In the ultrasonic image display area 63, positions where ROI 65 and maxIMT have been obtained (arrows in the drawing) are displayed together.

At step S25, if IMT measurement and other data measurements are further performed, the examiner pushes down the data measurement button 42a. Thereby, the measurement menu screen 4 shown in FIG. 3 is displayed, and the examiner may push down or select a predetermined button according to the screen display to perform the same or another data measurement.

As explained above, in the embodiment, since image processing (preprocessing) is performed on the data corresponding to the ROI being displayed on the screen and IMT is calculated based on the processed data, IMT measurement can be appropriately and correctly performed. In this regard, the range of preprocessed data is limited within the ROI, and thereby, the processing can be performed at a high speed. Further, in the embodiment, since plural combination patterns of measurement points are set with priorities, IMT measurement according to examiner's criterion and preference can be performed easily and efficiently. Furthermore, in the embodiment, since the amount of data is reduced by performing envelope detection processing or the like on waveforms represented by the RF data, the cost required for the cine-memory that stores the data can be suppressed.

Figure 10:
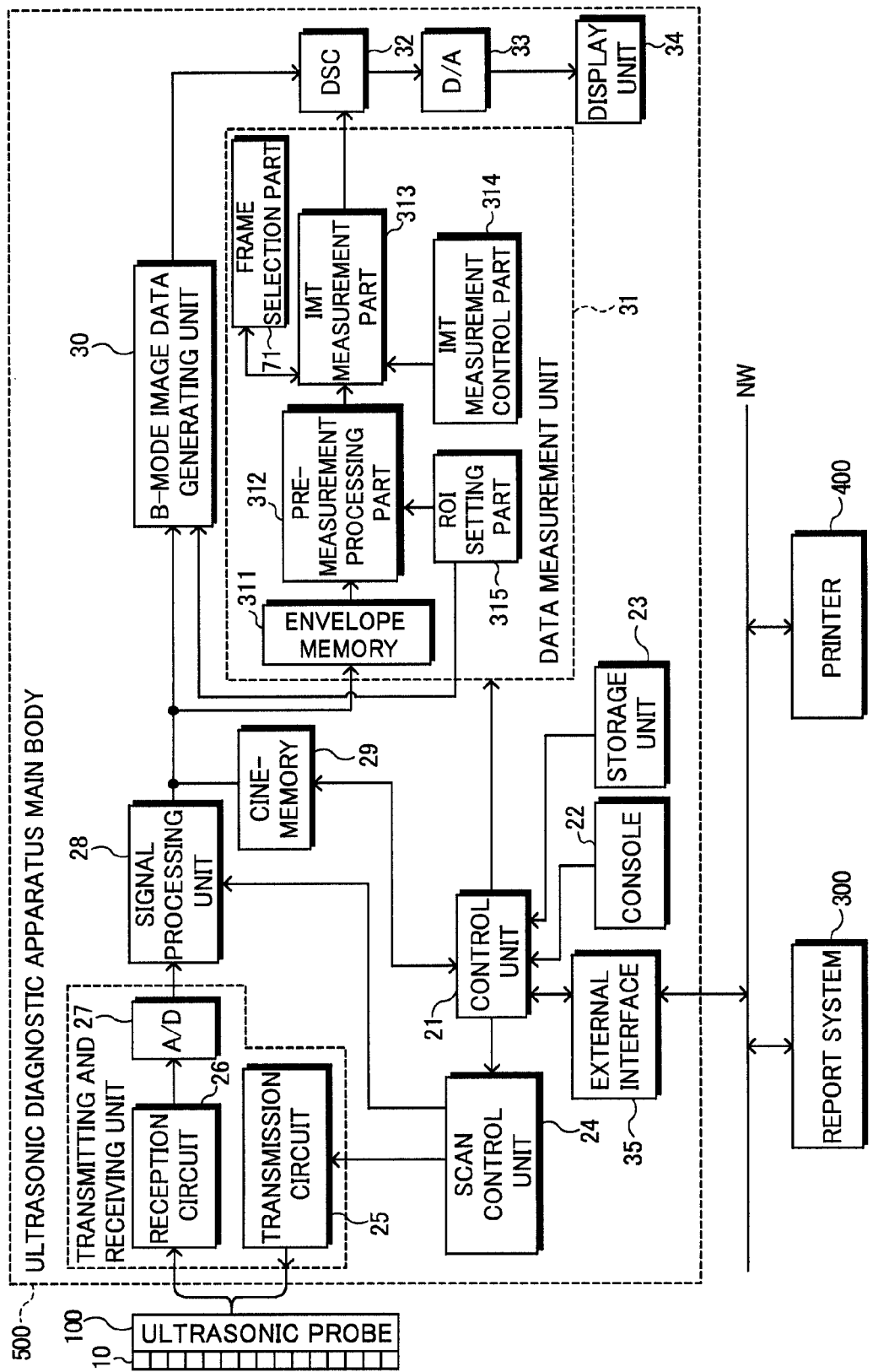
FIG. 10 is a block diagram showing a configuration of an ultrasonic diagnostic apparatus according to the second embodiment of the present invention.
Figure 11:
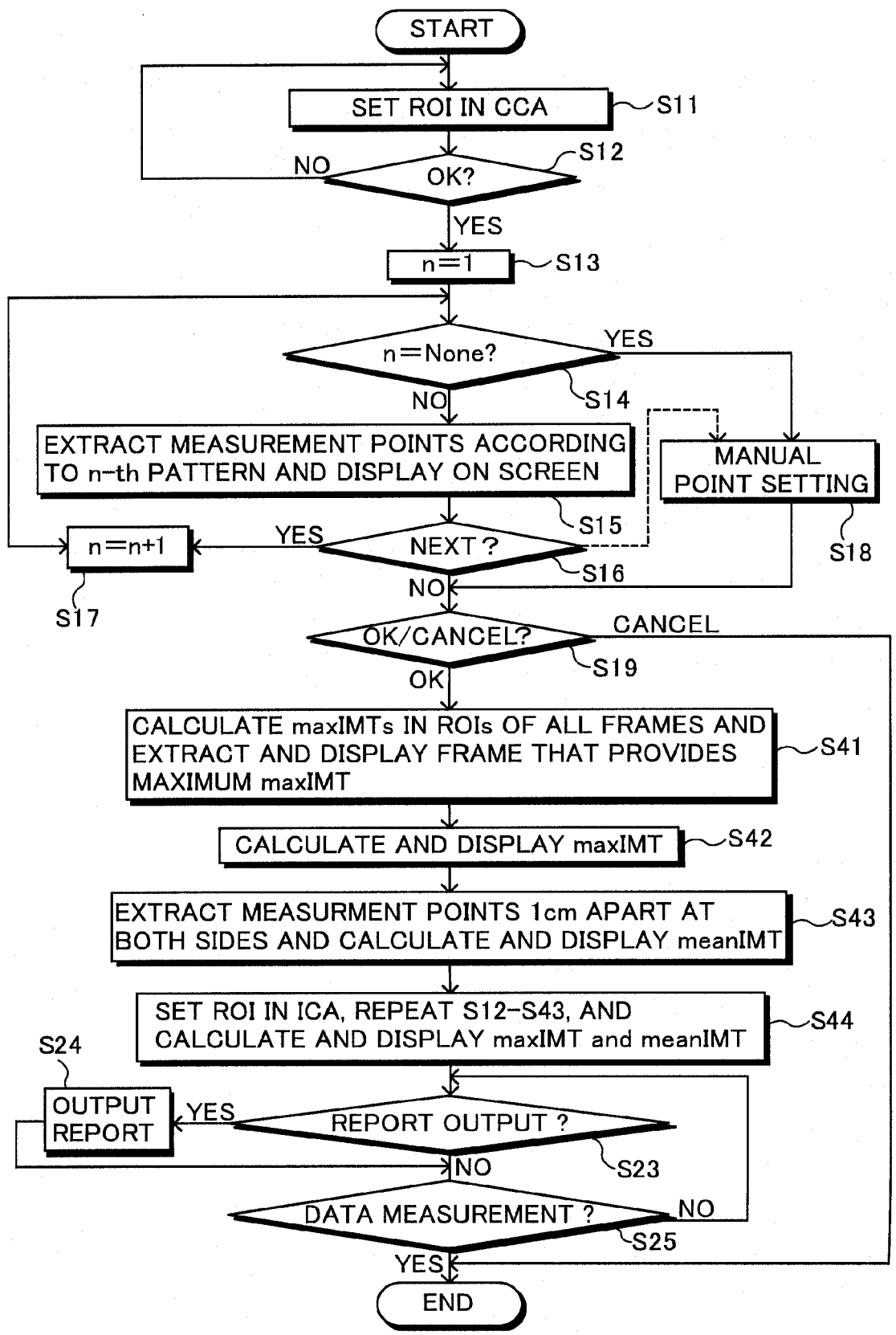
FIG. 11 is a flowchart showing an IMT measurement operation in the ultrasonic diagnostic apparatus according to the second embodiment of the present invention.

Next, an ultrasonic diagnostic apparatus according to the second embodiment of the present invention will be explained with reference to FIG. 10.

In the ultrasonic diagnostic apparatus according to the embodiment, an ultrasonic diagnostic apparatus main body 500 further has a frame selection part 71 compared to the ultrasonic diagnostic apparatus main body 200 shown in FIG. 1. When maxIMT is calculated with respect to each frame by the IMT measurement part 313, the frame selection part 71 accumulates them. Then, when IMT measurement ends with respect to all frames, the frame selection part 71 extracts a frame, that provides the maximum value of maxIMT, from among them. The rest of the configuration is the same as that shown in FIG. 1.

An operation of the ultrasonic diagnostic apparatus according to the embodiment will be explained with reference to FIGS. 10-12B.

First, the examiner starts IMT measurement after the priorities of combination patterns of measurement points have been set in advance. In response, at steps S11-S19 in FIG. 11, the IMT measurement part 313 extracts measurement points by automatic extraction or manual setting by a user. The operation of these steps is the same as that explained in the first embodiment.

Figure 12A:
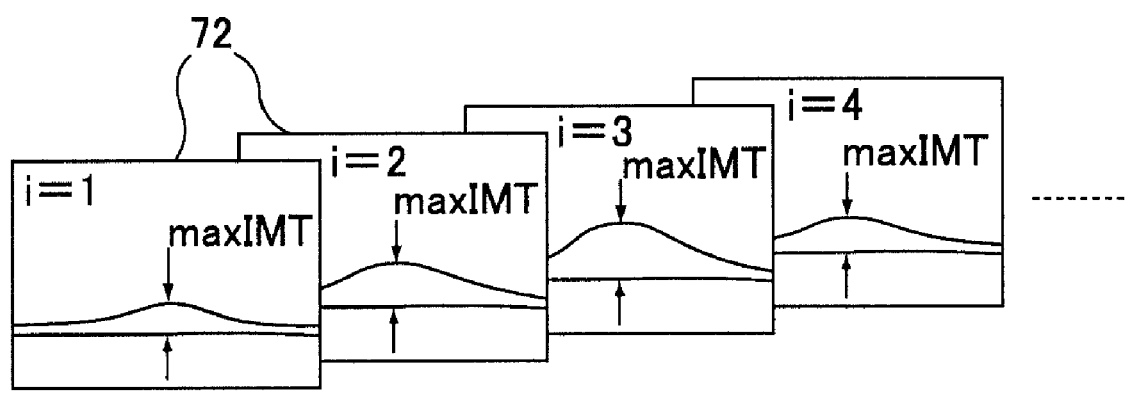
FIGS. 12A and 12B are diagrams for explanation of an operation of a frame selection part shown in FIG. 10.

Then, at step S41, as shown in FIG. 12A, the IMT measurement part 313 uses the extracted measurement points to calculate maxIMTs in plural frames (i=1, 2, 3, . . . ) stored in the cine-memory 29 or the envelope memory 311. Those values are accumulated in the frame selection part 71. When the computation on a predetermined number of frames ends, the frame selection part 71 selects the frame that provides the maximum maxIMT from among the frames and outputs it to the IMT measurement part 313.

Figure 12B:
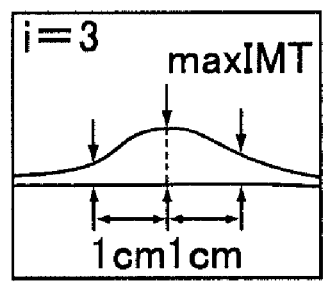

As shown in FIG. 12B, the IMT measurement part 313 calculates maxIMT in the frame outputted from the frame selection part 71 and outputs it (step S42), extracts IMTs at points 1 cm apart at both sides of the maxIMT based on the value of maxIMT and the position where maxIMT has been acquired, and calculates the mean value meanIMT of the IMTs at those points and outputs it (step S43).

Then, at step S44, the IMT measurement part 313, the IMT measurement control part 314, and the frame selection part 71 obtain the value of maxIMT and the value of mean IMT in the frame where the maxIMT is the maximum with respect to ICA in the same manner as at steps S11-S43. Furthermore, at steps S23-S25, the control unit 21 outputs IMT measurement results as reports to the report system 300 or the like according to the user's operation.

As explained above, according to the embodiment, since the section where maxIMT is the maximum is selected and the maxIMT on the section is calculated, the diagnostic accuracy for arteriosclerosis and so on can be improved.

Figure 13:
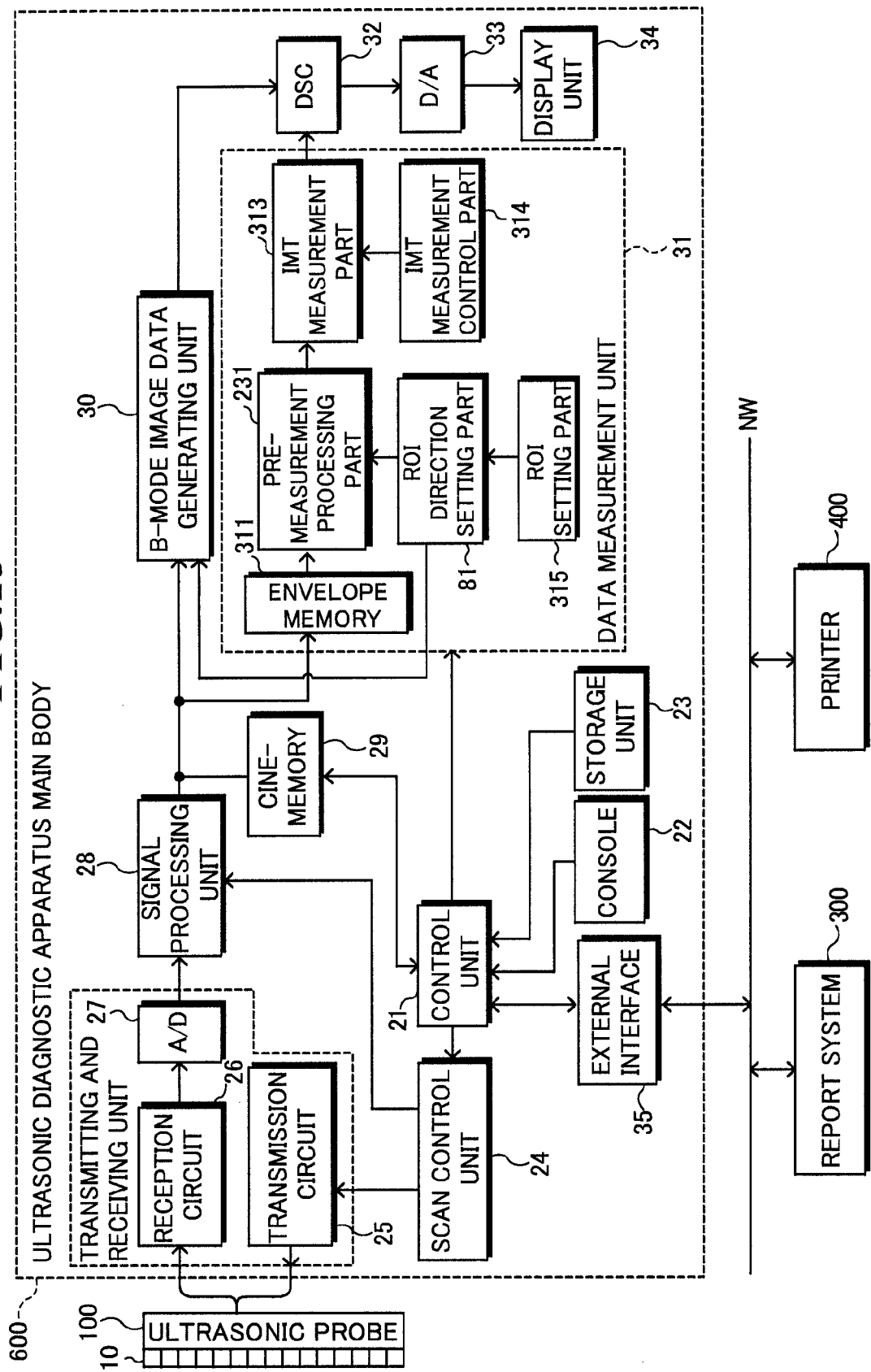
FIG. 13 is a block diagram showing a configuration of an ultrasonic diagnostic apparatus according to the third embodiment of the present invention.

Next, an ultrasonic diagnostic apparatus according to the third embodiment of the present invention will be explained with reference to FIG. 13.

In the ultrasonic diagnostic apparatus according to the embodiment, an ultrasonic diagnostic apparatus main body 600 further has an ROI direction setting part 81 compared to the ultrasonic diagnostic apparatus main body 200 shown in FIG. 1. The ROI direction setting part 81 rotates ROI set by the ROI setting part 315 according to the examiner's operation. The rest of the configuration is the same as that shown in FIG. 1.

An operation of the ultrasonic diagnostic apparatus according to the embodiment will be explained with reference to FIGS. 13-15B.

Figure 15A:
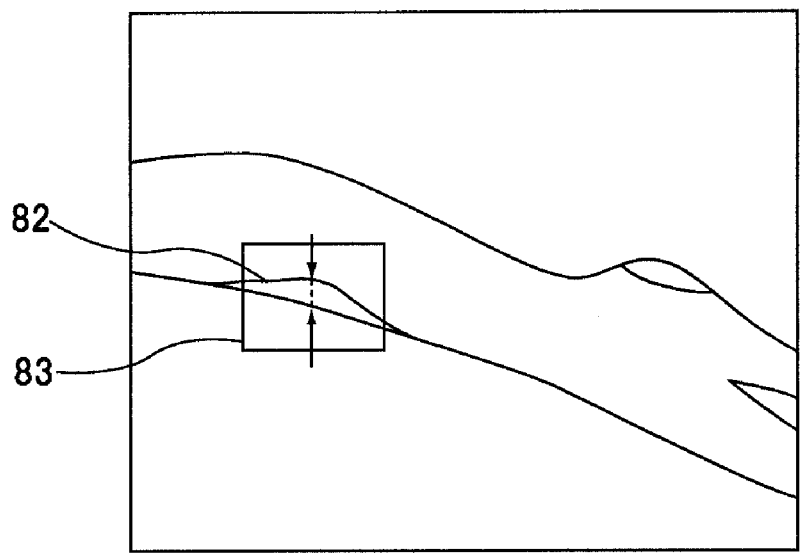
FIGS. 15A and 15B are diagrams for explanation of an operation of an ROI direction setting part shown in FIG. 13.

First, the examiner starts IMT measurement after the priorities of combination patterns of measurement points have been set in advance. Then, at steps S11-S12 in FIG. 14, as shown in FIG. 15A, the ROI setting part 315 sets ROI 83 in a region of interest (e.g., a plaque 82) in CCA according to user's operation. The detailed operation at these steps is the same as that explained in the first embodiment.

As described above, the direction of measurement lines of IMT is fixed relative to the side (depth direction) of ROI. Accordingly, as shown in FIG. 15A, when the measurement lines are slanted relative to the thickness direction of vessel wall, correct IMT measurement becomes impossible.

Figure 15B:
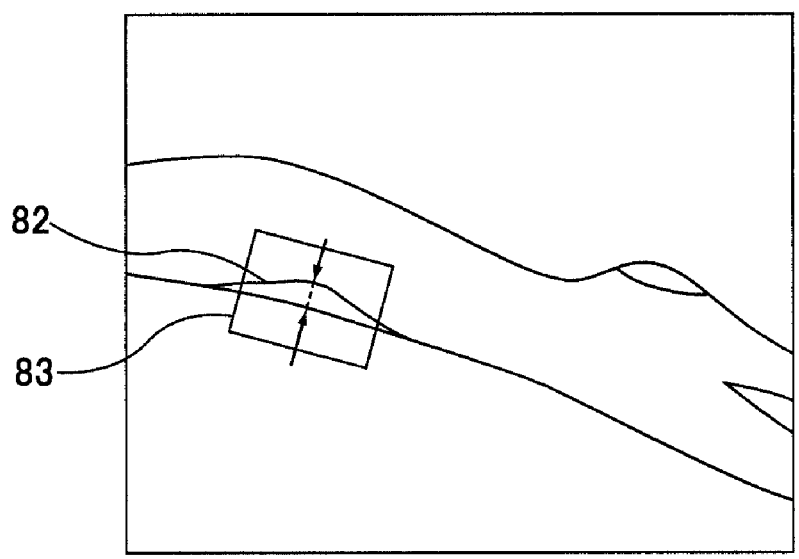
Figure 16:
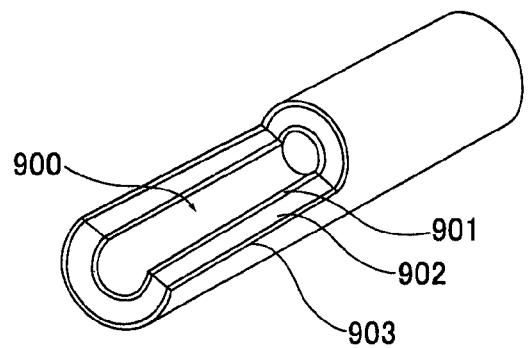
FIG. 16 is a diagram for explanation of an artery structure.
Figure 17:
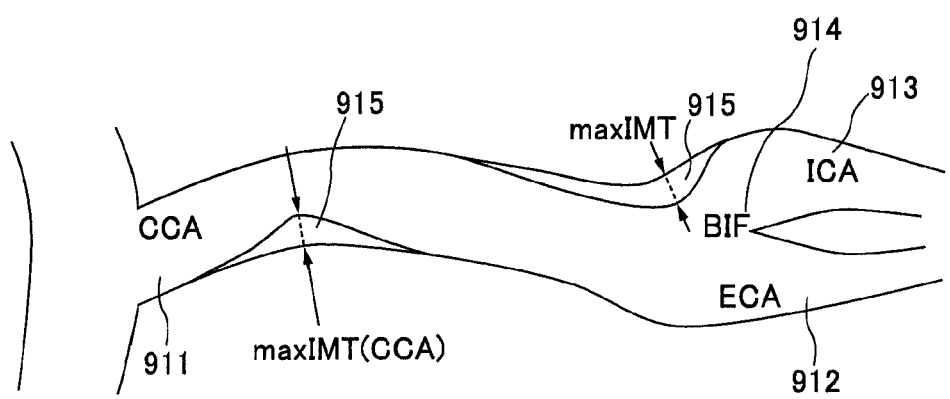
FIG. 17 shows a carotid artery shape and a measurement position of maxIMT.
Figure 18:
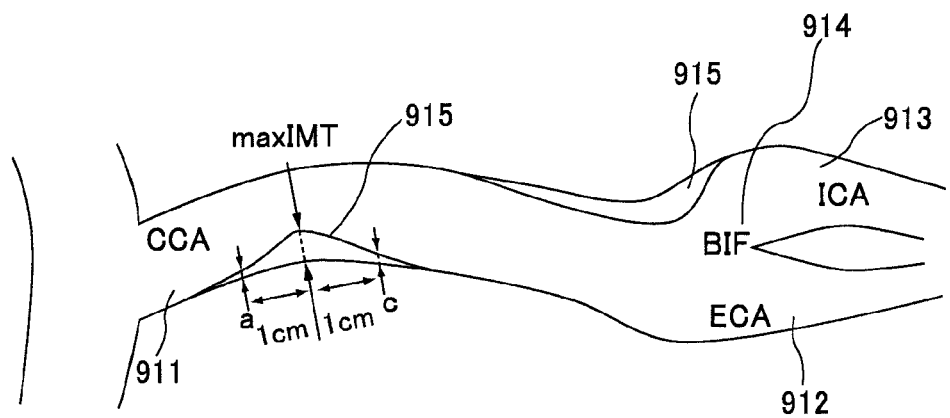
FIG. 18 shows the carotid artery shape and a measurement position of meanIMT.

Accordingly, at step S51, the examiner rotates the ROI 83 by using the track ball 42c (FIG. 2) and so on, such that the measurement line is nearly in parallel with the real thickness direction of IMT, i.e., the measurement line is nearly perpendicular to the length direction of vessel wall. Thereby, as shown in FIG. 15B, the measurement line is perpendicular to the thickness direction of vessel wall. At step S52, if the examiner judges that the direction of ROI 81 is appropriate, the examiner pushes down the OK button 42e. Thereby, the position and direction of ROI 81 are determined.

Furthermore, as explained in the first embodiment, at steps S13-S25, the IMT measurement part 313 measures maxIMT and mean IMT in CCA and ICA, and outputs them. In this regard, measurement points are extracted along the measurement line determined according to the rotation angle of the ROI 83.

As explained above, according to the embodiment, since the ROI is rotated to direct the measurement line along the thickness direction of IMT, IMT can be measured more correctly. Furthermore, in the embodiment, the pre-measurement processing part 312 may change the direction, in which image processing such as smoothing processing is performed, according to the rotation angle of the ROI. By performing image processing according to the measurement line direction, the accuracy of IMT measurement can be further improved.

In the above-explained first to third embodiments, the mean value at the three points around the position of maxIMT is calculated as meanIMT. However, the mean value of IMTs within a predetermined range including the position of maxIMT may be calculated as meanIMT. Since variations in mean value can be reduced by increasing the measurement points, the accuracy of medical diagnoses can be further improved.

The invention claimed is:

1. An ultrasonic diagnostic apparatus comprising:
    an ultrasonic probe for transmitting ultrasonic waves to an object to be inspected and receiving ultrasonic echoes generated by reflection of the ultrasonic waves in the object to output reception signals;
    a signal processing unit for performing at least envelope detection processing on the reception signals outputted from said ultrasonic probe to generate envelope data;
    an image data generating unit for generating image data representing an ultrasonic image on the object based on the envelope data;
    a pre-measurement processing part for performing structural image generating processing on the envelope data;
    an operation unit to be used for presetting plural combination patterns of measurement points to be extracted to measure a distance between a first peak, which appears when ultrasonic waves are reflected at a boundary between a vascular lumen and an intima, and a second peak, which appears when ultrasonic waves are reflected at a boundary between a media and an adventitia, from among local minimum points, local maximum points, and midpoints between the local minimum points and the local maximum points of the envelope data, and for presetting priorities of the plural combination patterns; and
    a measurement part for extracting a pair of measurement points from the envelope data processed by said pre-measurement processing part according to a combination pattern of measurement points selected from among the plural combination patterns of measurement points in order of the priorities of the plural combination patterns, and measuring an IMT (intima media thickness) of a blood vessel based on coordinates of the extracted pair of measurement points.

2. The ultrasonic diagnostic apparatus according to claim 1, further comprising:
    a ROI (region of interest) setting part for setting a ROI in the ultrasonic image represented by the image data generated by said image data generating unit;
    wherein said pre-measurement processing part performs structural image generating processing on the envelope data corresponding to the ROI set by said ROI setting part.

3. The ultrasonic diagnostic apparatus according to claim 1, wherein said pre-measurement processing part performs structural image generating processing on the envelope data by obtaining a signal representing average values of (i) a signal representing local maximum points of the envelope data and (ii) a signal representing local minimum points of the envelope data.

4. A data measurement method to be used in an ultrasonic diagnostic apparatus for transmitting ultrasonic waves to an object to be inspected and receiving ultrasonic echoes generated by reflection of the ultrasonic waves in the object to obtain reception signals and performing at least envelope detection processing on the reception signals to generate envelope data, said method comprising the steps of:
   (a) generating image data representing an ultrasonic image on the object based on the envelope data;
   (b) performing structural image generating processing on the envelope data; and
   (c) extracting a pair of measurement points from the envelope data processed at step (b) according to a combination pattern of measurement points selected from among plural combination patterns of measurement points, which are preset by using an operation unit, to be extracted to measure a distance between a first peak, which appears when ultrasonic waves are reflected at a boundary between a vascular lumen and an intima, and a second peak, which appears when ultrasonic waves are reflected at a boundary between a media and an adventitia, from among local minimum points, local maximum points, and midpoints between the local minimum points and the local maximum points of the envelope data, in order of priorities of the plural combination patterns, which are preset by using said operation unit, and measuring an IMT (intima media thickness) of a blood vessel based on coordinates of the extracted pair of measurement points.

5. The data measurement method according to claim 4, further comprising the step of:
   (d) setting a ROI (region of interest) in the ultrasonic image represented by the image data generated at step (a);
   wherein step (b) includes performing structural image generating processing on the envelope data corresponding to the ROI set at step (d).

6. The data measurement method according to claim 4, wherein step (b) includes performing structural image generating processing on the envelope data by obtaining a signal representing average values of (i) a signal representing local maximum points of the envelope data and (ii) a signal representing local minimum points of the envelope data.

7. A data measurement program embodied in non-transitory form on a computer readable medium, to be used in an ultrasonic diagnostic apparatus for transmitting ultrasonic waves to an object to be inspected and receiving ultrasonic echoes generated by reflection of the ultrasonic waves in the object to obtain reception signals and performing at least envelope detection processing on the reception signals to generate envelope data, said program actuating a CPU to execute the procedures of:
   (a) generating image data representing an ultrasonic image on the object based on the envelope data;
   (b) performing structural image generating processing on the envelope data; and
   (c) extracting a pair of measurement points from the envelope data processed at procedure (b) according to a combination pattern of measurement points selected from among plural combination patterns of measurement points, which are preset by using an operation unit, to be extracted to measure a distance between a first peak, which appears when ultrasonic waves are reflected at a boundary between a vascular lumen and an intima, and a second peak, which appears when ultrasonic waves are reflected at a boundary between a media and an adventitia, from among local minimum points, local maximum points, and midpoints between the local minimum points and the local maximum points of the envelope data, in order of priorities of the plural combination patterns, which are preset by using said operation unit, and measuring an IMT (intima media thickness) of a blood vessel based on coordinates of the extracted pair of measurement points.

8. The data measurement program according to claim 7, further actuating the CPU to execute the procedure of:
   (d) setting a ROI (region of interest) in the ultrasonic image represented by the image data generated at procedure (a);
   wherein procedure (b) includes performing structural image generating processing on the envelope data corresponding to the ROI set at procedure (d).

9. The data measurement program according to claim 7, wherein procedure (b) includes performing structural image generating processing on the envelope data by obtaining a signal representing average values of (i) a signal representing local maximum points of the envelope data and (ii) a signal representing local minimum points of the envelope data.

* * * * *